(12) United States Patent
Hilbert et al.

(10) Patent No.: US 11,587,675 B2
(45) Date of Patent: Feb. 21, 2023

(54) QUANTITATIVE MAPPING BY DATA-DRIVEN SIGNAL-MODEL LEARNING

(71) Applicant: SIEMENS HEALTHCARE GMBH, Erlangen (DE)

(72) Inventors: Tom Hilbert, Lausanne (CH); Tobias Kober, Lausanne (CH)

(73) Assignee: Siemens Healthcare GmbH, Erlangen (DE)

( * ) Notice: Subject to any disclaimer, the term of this patent is extended or adjusted under 35 U.S.C. 154(b) by 909 days.

(21) Appl. No.: 16/426,486

(22) Filed: May 30, 2019

(65) Prior Publication Data
US 2019/0371465 A1   Dec. 5, 2019

(30) Foreign Application Priority Data
May 30, 2018   (EP) ..................................... 18175213

(51) Int. Cl.
| | |
|---|---|
| *G16H 50/20* | (2018.01) |
| *G06N 20/00* | (2019.01) |
| *G06F 16/28* | (2019.01) |
| *G06F 16/22* | (2019.01) |
| *G06N 3/08* | (2023.01) |

(52) U.S. Cl.
CPC ........... *G16H 50/20* (2018.01); *G06F 16/288* (2019.01); *G06N 20/00* (2019.01); *G06F 16/22* (2019.01); *G06N 3/08* (2013.01)

(58) Field of Classification Search
CPC .......... G16H 50/20; G06N 20/00; G06N 3/08; G06F 16/288; G06F 16/22
USPC .......................................................... 706/12
See application file for complete search history.

(56) References Cited

U.S. PATENT DOCUMENTS

| | | | | |
|---|---|---|---|---|
| 7,096,206 | B2 * | 8/2006 | Hitt .......................... | G06N 3/08 706/932 |
| 7,542,947 | B2 * | 6/2009 | Guyon .................. | G06K 9/6231 707/999.006 |
| 10,846,616 | B1 * | 11/2020 | Busbridge .............. | G06N 3/006 |
| 11,037,073 | B1 * | 6/2021 | Watkins .............. | G06F 3/04847 |

(Continued)

OTHER PUBLICATIONS

Deep Learning for Magnetic Resonance Fingerprinting Elisabeth Hoppe et al. (pp. 202-206) 2017.*

(Continued)

*Primary Examiner* — Tauqir Hussain
(74) *Attorney, Agent, or Firm* — Laurence A. Greenberg; Werner H. Stemer; Ralph E. Locher

(57) ABSTRACT

A system and a method determine a value for a parameter. Reference values for the parameter are determined from a group of objects. A first technique is used by the system for determining for each object the reference value from a first set of data. A learning dataset is created by associating for each object of the group of objects a second set of data and the reference value. The second set of data is acquired by the system according to a second technique for determining values of the parameter and is configured for enabling a determination of the parameter. A machine learning technique trained on the learning dataset is used for determining a value of the parameter. The second set of data obtained for each of the objects is used as input in a machine learning algorithm and its associated reference value is used as output target.

12 Claims, 2 Drawing Sheets

(56) References Cited

U.S. PATENT DOCUMENTS

| | | | |
|---|---|---|---|
| 2005/0071300 A1* | 3/2005 | Bartlett | G06N 20/10 706/12 |
| 2009/0132443 A1* | 5/2009 | Mueller | G06N 7/005 706/14 |
| 2010/0063948 A1* | 3/2010 | Virkar | G06N 20/10 707/769 |
| 2010/0205124 A1* | 8/2010 | Ben-Hur | G06V 10/7715 706/12 |
| 2012/0041911 A1* | 2/2012 | Pestian | G16H 50/30 706/45 |
| 2013/0116519 A1* | 5/2013 | Wood | A61B 5/0059 600/322 |
| 2014/0156573 A1* | 6/2014 | Szyperski | G01R 33/4625 706/12 |
| 2014/0227196 A1* | 8/2014 | Zhang | A61K 49/106 424/9.362 |
| 2014/0279721 A1* | 9/2014 | Siegel | G16B 50/00 706/11 |
| 2015/0220838 A1* | 8/2015 | Martin | G16B 40/30 706/12 |
| 2015/0276903 A1* | 10/2015 | Taniguchi | G01R 33/5614 324/318 |
| 2015/0317444 A1* | 11/2015 | Backhed | G16H 50/70 706/46 |
| 2016/0195526 A1* | 7/2016 | Venkatesan | G01N 33/54326 435/7.1 |
| 2017/0035916 A1* | 2/2017 | Amir | A61K 49/0021 |
| 2017/0269174 A1* | 9/2017 | Rothgang | G01R 33/5611 |
| 2017/0372229 A1* | 12/2017 | Ura | G06N 20/00 |
| 2018/0217220 A1* | 8/2018 | Gulani | G01R 33/5676 |
| 2018/0231626 A1* | 8/2018 | Gulani | G01R 33/5602 |
| 2018/0336677 A1* | 11/2018 | Sloan | G06T 7/0012 |
| 2019/0080235 A1* | 3/2019 | Maruhashi | G06N 3/08 |
| 2019/0080236 A1* | 3/2019 | Maruhashi | G06K 9/6262 |
| 2019/0122144 A1* | 4/2019 | Kabeya | H04L 63/1408 |
| 2019/0328231 A1* | 10/2019 | Song | G01R 33/5608 |
| 2019/0371465 A1* | 12/2019 | Hilbert | G06N 20/00 |
| 2019/0378619 A1* | 12/2019 | Meyer | G16H 50/70 |
| 2020/0069257 A1* | 3/2020 | Fleming | G06T 11/005 |
| 2020/0256856 A1* | 8/2020 | Chou | G01N 15/06 |
| 2020/0334524 A1* | 10/2020 | Sprague | G06N 3/08 |
| 2021/0012087 A1* | 1/2021 | Purcell | G01N 21/17 |
| 2021/0149005 A1* | 5/2021 | Wang | G01R 33/5608 |
| 2021/0279643 A1* | 9/2021 | Koduru | G06F 11/3447 |

OTHER PUBLICATIONS

Rapid and Direct Quantification of Longitudinal Time Bagher et al. (pp. 236-240) Jun. 14, 2009.*

Q-Space Deep Learning Golkov et al. (pp. 1344-1351) May 2016.*

Ben-Eliezer, Noam et al.: "Rapid and Accurate T2 Mapping from Multi-Spin-Echo Data Using Bloch-Simulation-Based Reconstruction"; Magnetic Resonance in Medicine; vol. 73; pp. 809-817; 2015; DOI: 10.1002/mrm.25156.

Lukzen N.N. et al.: "The generating functions formalism for the analysis of spin response to the periodic trains of RF pulses. Echo sequences with arbitrary refocusing angles and resonance offsets"; Journal of Magnetic Resonance; vol. 196; pp. 164-196; 2009; doi: 10.1016/j.jmr.2008.11.008.

Look D. C. et al.: "Time Saving in Measurement of NMR and EPR Relaxation Times"; Review of Scientific Instruments; vol. 41; No. 2; pp. 250-251; 1970; https://doi.org/10.1063/1.1684482.

Cloos, Martijn A. et al. "Multiparametric imaging with heterogeneous radiofrequency fields" Nature Communications, vol. 7, No. 12445, Aug. 16, 2016 // DOI: 10.1038/ncomms12445.

Kecskemeti, Steven et al.: "MPnRAGE: A Technique to Simultaneously Acquire Hundreds of Differently Contrasted MPRAGE Images with Applications to Quantitative T1 Mapping"; Magnetic Resonance in Medicine; vol. 75; pp. 1040-1053; 2016; DOI: 10.1002/mrm.25674.

Sumpf, Tilman J. et al.: "Fast T2 Mapping With Improved Accuracy Using Undersampled Spin-Echo MRI and Model-Based Reconstructions With a Generating Function"; IEEE Transactions on Medical Imaging; vol. 33; No. 12; 2014; DOI: 10.1109/TMI.2014.2333370.

Ma, Dan et al. "Magnetic resonance fingerprinting" Nature, vol. 495, pp. 187-192, 2013//doi:10.1038/nature11971/Mar. 14, 2013.

Golkov, Vladimir et al. "q-Space Deep Learning: Twelve-Fold Shorter and Model-Free Diffusion MRI Scans" IEEE Transactions on Medical Imaging, vol. 35, No. 5, pp. 1344-1351, May 2016 // XP011607959; ISSN: 0278-0062; DOI:10.1109/TMI.2016.2551324, [retrieved on Apr. 29, 2016], Abstract, Sections I.A., II. and III.; figures 2,6.

* cited by examiner

QUANTITATIVE MAPPING BY DATA-DRIVEN SIGNAL-MODEL LEARNING

CROSS-REFERENCE TO RELATED APPLICATION

This application claims the priority, under 35 U.S.C. § 119, of European application EP 18175213.0, filed May 30, 2018; the prior application is herewith incorporated by reference in its entirety.

BACKGROUND OF THE INVENTION

Field of the Invention

The present disclosure is directed, in general, to imaging techniques for imaging biological tissues, and more specifically to quantitative imaging in magnetic resonance imaging (MRI).

The contrast apparent in images acquired through classical MRI is the result of a combination of different physical parameters of underlying tissue(s), the particular MRI acquisition technique and its parameters.

An approach for acquiring MR-based information on biological tissue is to directly measure one or more of its underlying physical properties, e.g. the tissue-specific T1 and T2 relaxation constants or the proton density PD. Those quantitative techniques are usually referred to as "parametric mapping" or "quantitative imaging" methods. Using this approach, the resulting image contrasts become more independent from the employed hardware, the applied imaging technique and the particular imaging parameters, because they directly probe the properties of the tissue. This facilitates comparability and thus clinical diagnosis and may enable building up a database of normal parametric values to which a newly scanned patient dataset can be compared. In other words, it provides the means to move from relative contrast information depending on many different factors towards an absolute measure of one or more separate physical properties.

In quantitative MRI, images encoding the quantitative parameters of interest are typically sampled multiple times, e.g. at different echo times using a multi-echo spin-echo (MESE) sequence to estimate the transverse relaxation time T2. Subsequently, a signal model describing the relation between image intensities and relevant tissue properties is fitted onto these series of images (in the case of the MESE sequence that could e.g. be a simple mono-exponential T2-signal decay model), yielding a quantitative map. The chosen signal model is an approximation of reality by nature and may omit important components that drive the signal behavior beyond the quantitative parameter of interest due to the complex nature of the tissue microstructure (e.g. magnetization transfer effects) or system imperfections (e.g. field inhomogeneity), among others. Taking MESE-based T2 mapping as an example, one often consciously ignores sources of model failure resulting from non-ideal pulse profiles inducing stimulated echoes that cannot be described with a simple mono-exponential decay. As a result of this omission, T2 values are systematically overestimated in comparison to a gold-standard sequence (e.g. single-echo spin-echo sequence). There is noteworthy a trade-off between the complexity of the employed signal model and the precision of the obtained quantitative maps as well as the robustness of the signal model fitting.

In the past years, more complex signal models have been developed to describe the behavior of the magnetization more accurately. In the example introduced above, performing T2 mapping with a MESE MRI sequence, a more detailed signal model uses a more complex analytical model known as "generating function" and incorporates one of the sources of error—the stimulated echoes—into the model (see for instance Lukzen et al., J. Magn. Reson. 2009, 196(2): 164-169), or Sumpf et al., IEEE Trans. Med. Imaging 2014, 33(12): 2213-2222). Although the generating function describes the relation between image intensities and relevant tissue properties better, it is more difficult to fit to the image series since the model has more independent variables, i.e. more mathematical degrees of freedom. Thus, additional regularization terms are often required to allow fitting of this ill-posed problem, which is usually tuned by yet more variables/regularization weights.

Alternatively, the problem was addressed by replacing the analytical signal model with simulations and using dictionary fitting (e.g. Bloch or Extended-Phase-Graph simulations—see for instance Ben-Eliezer et al, Magn. Reson. Med. 2015, 73(2): 809-817, or Ma et al., Nature 2013, 495(7440): 187-192). However, similar to the more complex analytical solutions, the simulations have a large number of independent variables, leading to a significantly increased numerical complexity which requires high computing powers or might not even be solvable at all with today's hardware. To address these limitations, some variables are often set to a fixed value introducing assumptions into the model which might not be in line with reality.

Both analytical solutions and simulations are based on the current understanding of MR physics and tissue microstructure, where the complex physical interactions of the latter are not fully understood in every detail today. Consequently, it might today not even be possible to correctly fit the above-mentioned parameters correctly.

Noteworthy, to validate a given model, the quantitative values obtained with this model are compared to gold-standard values, i.e. reference values. These gold-standard values can be obtained from MRI measurements using acquisition schemes that are typically very long and hence not applicable in clinical or even clinical research practice.

SUMMARY OF THE INVENTION

An objective of the present invention is to propose an efficient and simple method and system for the quantitative mapping of biological tissue.

For achieving the objective, the present invention proposes to use a machine learning method and system for determining parameters characterizing biological tissues as disclosed in the objects of the independent claims. Other advantages of the invention are presented in the dependent claims.

The present invention proposes notably to learn a relation between a) a signal intensity measured by a system (typically a medical device) or signal data acquired by the system for determining a parameter (or a quantitative value) or measuring a parameter characterizing a biological tissue or organ, and b) a gold-standard value of the parameter, using machine learning tools and techniques rather than a predefined physical model as currently used in prior art techniques. To this end, gold-standard data is used to train the machine learning method and system according to the invention. Advantageously, the method and system according to the invention are model-free method and system, and enable purely signal-driven modeling and subsequent generation of parametric maps for the parameter, potentially incorporating unwanted "dirt effects" in the learnt model in a way not possible with a predefined signal prior art model.

In particular, the present invention concerns a machine learning method for measuring or determining a parameter which might be characterized by a quantitative value and enables a characterization of a biological tissue, the parameter being for instance a physical parameter (as T1 or T2) or a biological parameter. The method includes:

a) determining reference values for the parameter from a group of objects, wherein each reference value is the value of the parameter determined from a first set of data (e.g. a first set signal intensities) measured by a system, e.g. a medical device, for at least one of the objects according to a first technique, the first technique typically determining for each object the value of the parameter from fitting a signal model to the first set of data (e.g. said first signal intensities). According to the present invention, the object can be any material or matter that can be characterized by the parameter under investigation, for instance living matter, a patient, or a subject, the object encompassing also phantom, histology or animal data, and can be therefore also a data object from which said reference values might be determined;

b) creating a learning dataset by associating for each object a second set of data (e.g. a second set of signal intensities or signal data) enabling the determination of the parameter and the reference value previously determined from the first set of data using the first technique, wherein the second set of data is acquired by the system according to a second technique for determining values of the parameter;

c) using a machine learning technique, in particular implemented by the system, trained on the learning dataset for determining a value of the parameter, wherein the second set of data determined or measured for each of the objects is used as input in a machine learning algorithm and its associated reference value is used as output target for said machine learning algorithm;

d) determining a relationship between the second set of data and a value of the parameter obtained for each object by training the machine learning algorithm on the learning dataset obtained from the group of objects;

e) using, for a new object, the relationship to determine a value for the new object parameter from another set of data obtained by means of the second technique, e.g. another set of signal intensities measured or determined by means of the second technique.

The present invention concerns also a system configured for implementing the previously described machine learning method. The system includes at least:

a) a processing unit capable of determining reference values for the parameter from the group of objects, wherein each reference value is the value of the parameter determined by the processing unit according to a first technique from a first set of data determined by the system for each of the objects, wherein the first technique typically determines the reference value from fitting the first set of data with a signal model;

b) a database for storing a learning dataset containing and associating for each object a second set of data and the reference value determined from said first set of data using the first technique, wherein the second set of data (e.g. second set of signal intensities) is acquired by the system according to a second technique for determining values of the parameter;

c) the processing unit of the claimed system being further configured:

c1) for using a machine learning technique trained on the learning dataset for determining a value for the parameter from the second set of data for each of the objects, wherein the second set of data obtained for each of the objects is used as input in a machine learning algorithm and its associated reference value is used as output target for the machine learning algorithm;

c2) for determining a relationship between the second set of data and values of the parameter obtained for each object by training the machine learning algorithm on the learning dataset obtained for the group of objects; and c3) using, for a new object, the relationship to determine a value of the new object parameter from another set of data obtained by the system through the second technique. For instance, the system might be configured for measuring another set of signal intensities according to the second technique and using it as new input in the machine learning algorithm for calculating a value for the parameter for the new object.

Various disclosed embodiments include machine learning methods and corresponding systems and computer readable mediums for determining, for instance automatically determining, a value for a parameter from the relationship between a set of data acquired according to a second technique and a reference value acquired according to a first technique, wherein the relationship is obtained by training a machine learning algorithm on a learning dataset formed by said set of data and its corresponding reference value.

The foregoing has outlined rather broadly the features and technical advantages of the present disclosure so that those skilled in the art may better understand the detailed description that follows. Additional features and advantages of the disclosure will be described hereinafter that form the object of the claims. Those skilled in the art will appreciate that they may readily use the concept and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

Other features which are considered as characteristic for the invention are set forth in the appended claims.

Although the invention is illustrated and described herein as embodied in a quantitative mapping by data-driven signal-model learning, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
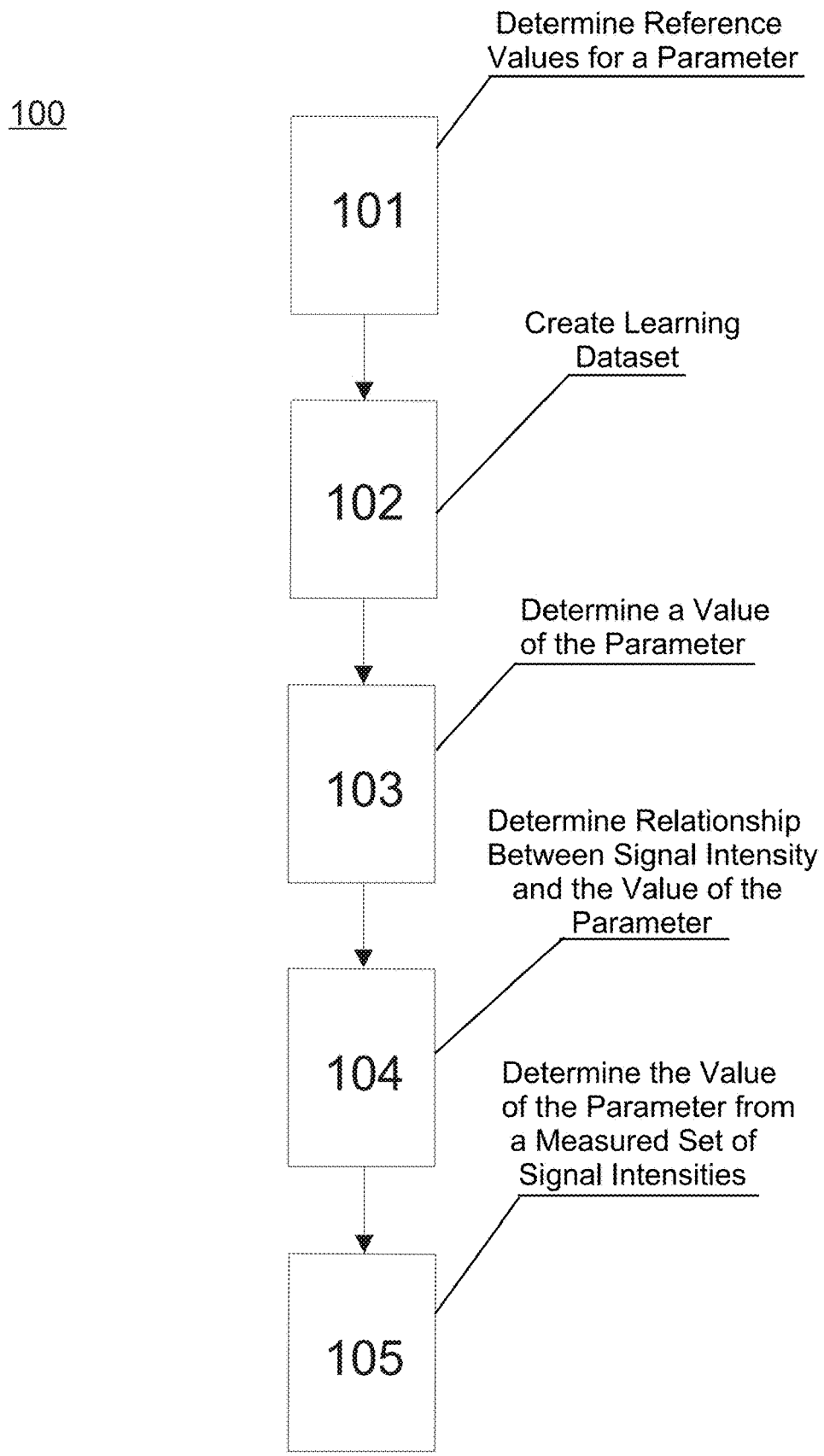
FIG. 1 is a flowchart of a machine learning method according to the invention.
Figure 2:
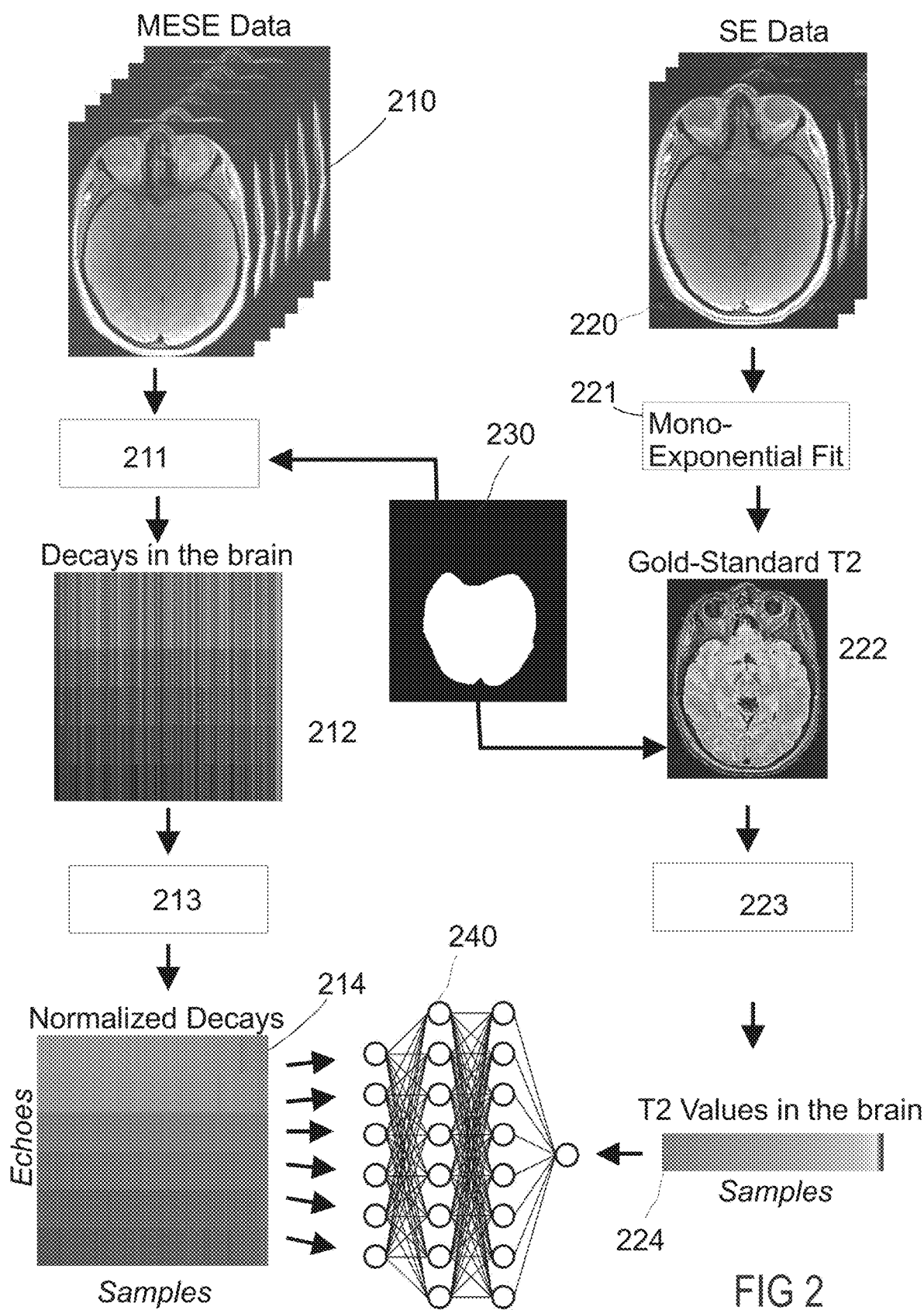
FIG. 2 is an illustration of another flowchart of the method according to the invention applied to MRI.

FIGS. 1 and 2, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged device. The numerous innovative teachings of the present application will be described with reference to exemplary non-limiting embodiments.

Referring now to the figures of the drawings in detail and first, particularly to FIG. 1 thereof, there is shown a machine learning method 100 for preferentially automatically determining a value (in particular a quantitative value) for a parameter, wherein determined values might be represented in a quantitative map, which enables characterizing a biological tissue of a patient. By characterizing, it has to be understood providing quantitative values regarding one or several biological tissue parameters, wherein the quantitative values may help a physician to determine whether the patient contains potentially pathologic tissue.

According to a preferred embodiment, the concept of the invention described in FIG. 1 is then applied to a specific, non-limiting, case of MRI, wherein an example of quantification of T2 using a learnt signal model for a MESE sequence 210 with a single-echo spin-echo (SE) sequence 220 as gold-standard reference is taken. In other words, in the preferred embodiment of FIG. 2, the first technique according to the invention uses a SE sequence 220 for quantifying T2 according to classical process and the second technique uses a MESE sequence 210 for quantifying T2 using a machine learning technique wherein the quantified T2 values obtained from the first technique are used as target output for the machine learning technique.

At step 101, reference values for a parameter are determined by the system according to the invention from a group of objects, for instance a group of subjects. The parameter might be a physical parameter or a biological parameter. The reference values, also called gold-standard reference values, are values, preferentially quantitative values, of the parameter that are determined by the system according to a first technique. The first technique is typically a time consuming technique that cannot be applied as such during clinical diagnosis. According to the present invention, the first technique is only used to create a learning dataset. The first technique is typically a known technique wherein the first set of data corresponds to a first signal intensity (or signal data) acquired by the system according to the invention for each object, the system being further configured for determining the value of the parameter for each object by fitting the signal intensity with a signal model. Each determined value for the parameter is then used as a reference value within the machine learning technique.

In the particular case of MRI described in FIG. 2, the first signal intensity might be a SE signal intensity, and step 101 may comprise acquiring SE signal intensity (or data) for each object of the group of objects and determining quantitative gold-standard T2 values (T2 being thus the parameter whose values have to be determined) for each object from a single-slice, resolution- and orientation-matched single-echo spin-echo sequence. The gold-standard T2 values 222 are preferentially computed using a classical signal fitting 221 onto the spin-echo data.

At step 102, the system according to the invention creates a learning dataset by associating for each object a second set of signal intensities (which corresponds in that case to said second set of data) and the T2 reference value determined from the first signal intensity using the first technique. For instance, in the case illustrated by FIG. 2, a given gold-standard T2 reference value might be associated with a measured MESE signal evolution (i.e. signal decay) in a database. In particular, for each object, normalized signal decay 214 and gold-standard T2 value in the brain 224, preferentially obtained after application 223 of a brain mask 230 determined for each object, are stored in a database in order to create the learning dataset. In other words, the method according to the invention may comprise acquiring MESE signal intensities, for instance MESE images, from the group of objects. Preferentially, intracranial volume might be first segmented 211 to restrict the learning solely to brain tissue, wherein the object corresponding brain mask 230 is applied to the MESE data for this purpose. All MESE signal decays 212 are preferably normalized 213 by dividing the signal intensities by the L2-norm of the decay. The normalization of the signal decays, or more generally of data used as input within the machine learning algorithm, could be performed differently (different norm or different scale) depending on the used technique. The optional application of the brain mask 230 as previously described advantageously improves the final result.

At step 103, the system according to the invention uses a machine learning technique for determining the value of the parameter from the second set of signal intensities, wherein the machine learning technique comprises using a machine learning algorithm for determining the value, and training the machine learning algorithm on the learning dataset wherein for each object the second signal intensity is used as input and the associated reference value as output target. For instance, the machine learning algorithm might be an artificial neuronal network 240 that is trained using the signal intensities of each echo as input and the gold-standard T2 value as target output. Preferentially, the artificial neuronal network 240 may comprise two layers with each 8 neurons and a root-mean-squared error to the gold-standard T2 as cost function. The training is preferentially performed with data from all available objects, i.e. with whole data of the learning dataset.

At step 104, the system determines a relationship between the signal intensity and the value of the parameter obtained for each object from the training of the machine learning algorithm on the learning dataset. In the example of FIG. 2, the machine learning algorithm is typically used to learn the relationship between the decay and the T2 value.

At step 105, the system uses the relationship to determine the value of the parameter from a measured set of signal intensities for a new object. For instance and as illustrated in FIG. 2, in order to reconstruct a new dataset (e.g. coming from the new object), every decay is fed to the previously trained artificial neuronal network to estimate T2 in each voxel of the new dataset, resulting in the desired quantitative value for the parameter based on the data driven signal model.

Advantageously, the present invention proposes therefore to replace a fixed signal model with a learnt relationship between "true" values (i.e. based on the gold standard reference values) and the respective quantitative measurements can help eliminating many of the difficulties related to finding an appropriate model for a given problem. Additionally, the data-driven approach proposed here is able to learn potential dirt effects in the acquired signal intensity, which are typically hard to model or even, cannot be modeled at all according to prior art technique. Another advantage is that no a priori knowledge has to be imposed regarding the assumed interaction of the tissue microstructure and the underlying MR physics.

Advantageously, the application of a trained neural network is typically very fast, i.e. once the machine learning algorithm, like the artificial neuronal network 240 of FIG. 2, is trained, parametric maps can be obtained very quickly in contrast to typically slow fitting procedures.

As already mentioned above, the present invention is not restricted to the specific embodiment of FIG. 2, but might be without effort generalizable to other quantification or determination of parameters since only a set of datasets acquired through the so-called second technique and gold-standard reference data acquired through the so-called first technique are required. In particular, the first technique and the second technique according to the reference might be the same, or are two different techniques. Regarding the specific embodiment illustrated by FIG. 2, a different type of input data than a MESE dataset using a different sequence could be used as input for the machine learning algorithm. For example, quantitative T1 mapping could be realized with a fast sampling of multiple inversion times after applying an inversion pulse (e.g. multiple FLASH blocks per repetition after an inversion pulse—see for instance Kecskemeti et al., Magn. Reson. Med. 2016, 75(3): 1040-1053) or a look-locker sequence, while the gold standard data, i.e. reference value, could be obtained by established slower techniques (e.g. an IR-SE as gold standard as described in Look DC, Locker DR, Rev. Sci. Instrum. 1970, 41(2): 250-251). In another example, the invention could also be used for magnetic resonance fingerprinting (see Ma et al., Nature 2013, 495(7440): 187-192), where the fingerprint is the input and the multi-parametric values are outputs of the artificial neuronal network. Similarly, the gold-standard approach (i.e. SE data used according to the specific embodiment of FIG. 2) could be replaced with a different MRI sequence, other imaging technique (PET, CT, SPECT) or even other data (not in-vivo objects) such as phantom, animal or histology data (Biopsy, post-mortem imaging).

Finally, the concept of the present invention may not only apply to the determination of quantitative values for parameters by training the machine learning algorithm, but also to more biologically oriented parameters, like a myelin content at a given location of a brain, or an axonal density. Of course, the present invention is not restricted to brain imaging, and could be performed in all body parts or arbitrary specimen. The machine learning technique described in the present invention and sometimes also referred to as artificial intelligence or data science tool may also use different approaches like a linear regression, a non-linear regression, a convolutional neuronal networks.

The invention claimed is:

1. A machine learning method for determining a value for a parameter, the value enabling a characterization of a biological tissue, the method comprises the steps of:
   determining reference values for the parameter from a group of objects, wherein a first technique is used by a system for determining for each object a reference value from a first set of data, wherein the first technique includes a single-echo spin-echo (SE) sequence and the parameter is a T2 relaxation time;
   creating a learning dataset by associating for each said object of the group of objects a second set of data and the reference value previously determined from the first set of data, wherein the second set of data is acquired by the system according to a second technique for determining values of the parameter and is configured for enabling a determination of the parameter, wherein the first technique and the second technique are two different imaging acquisition techniques;
   using a machine learning technique trained on the learning dataset for determining the value of the parameter, wherein the second set of data obtained for each of the objects is used as an input in a machine learning algorithm and its associated reference value is used as an output target for the machine learning algorithm;
   determining a relationship between the second set of data and the value of the parameter obtained for each said object by training the machine learning algorithm on the learning dataset; and
   using the relationship for determining from another data set the value for the parameter of a new object, wherein the another dataset has been obtained by the system by means of the second technique.

2. The method according to claim 1, wherein the first technique further comprises fitting the first data set by means of a signal model.

3. The method according to claim 1, wherein the second technique includes a multi-echo spin-echo (MESE) sequence.

4. The method according to claim 1, wherein the second dataset includes MESE signal decays.

5. The method according to claim 4, which further comprises applying a brain mask to the MESE signal decays and to the first dataset.

6. The method according to claim 4, which further comprises normalizing the MESE signal decays.

7. The method according to claim 1, wherein the machine learning algorithm is an artificial neuronal network.

8. The method according to claim 1, wherein:
   the parameter is T1 relaxation time; and
   the second technique includes fast sampling of multiple inversion times after applying an inversion pulse in order to obtain the second data set.

9. The method according to claim 1, wherein the second technique includes magnetic resonance fingerprinting.

10. The method according to claim 1, wherein the object is a subject, a patient, phantom, histology or animal data.

11. The method according to claim 1, wherein the machine learning technique, is implemented by the system.

12. A system for determining a value for a parameter, the system comprising:
   a processing unit capable of determining reference values for the parameter from a group of objects, wherein a first technique is used by the system for determining for each object a reference value from a first set of data acquired by the system, wherein the first technique includes a single-echo spin-echo (SE) sequence and the parameter is a T2 relaxation time;
   a database storing a learning dataset containing and associating for each said object of said group of objects a second set of data and a previously determined reference value, the second set of data is acquired by the system according to a second technique for determining values of the parameter, wherein the first technique and the second technique are two different imaging acquisition techniques; and
   said processing unit further programmed to:
      use a machine learning technique trained on a learning dataset for determining the value for the parameter from the second set of data for each of the objects, wherein the second set of data obtained for each of the objects is used as an input in a machine learning algorithm and its associated reference value is used as an output target for the machine learning algorithm;
      determine a relationship between the second set of data and the value of the parameter obtained for each said object by training the machine learning algorithm on the learning dataset; and use the relationship for determining from another data set the value for the parameter of a new object, wherein the another dataset has been obtained by the system by means of the second technique.

\* \* \* \* \*